(12) United States Patent
Ivansons et al.

(10) Patent No.: US 6,852,231 B2
(45) Date of Patent: Feb. 8, 2005

(54) SPIN-HEMODIALYSIS ASSEMBLY AND METHOD

(75) Inventors: Ivars V. Ivansons, Wilmington, DE (US); Dudley W. C. Spencer, Wilmington, DE (US)

(73) Assignee: Denco, Inc., Wilmington, DE (US)

( * ) Notice: Subject to any disclaimer, the term of this patent is extended or adjusted under 35 U.S.C. 154(b) by 93 days.

(21) Appl. No.: 10/077,038

(22) Filed: Feb. 15, 2002

(65) Prior Publication Data

US 2003/0155312 A1 Aug. 21, 2003

(51) Int. Cl.[7] .............................................. B01D 33/00
(52) U.S. Cl. .................. 210/646; 210/91; 210/330; 210/321.68; 210/321.79; 210/488; 210/782; 494/36; 494/37; 604/6.09
(58) Field of Search ........................ 210/91, 324, 330, 210/321.68, 321.78, 321.79, 321.8, 321.88, 321.89, 645, 646, 650, 651, 780, 781, 782, 787; 604/6.01, 6.09; 494/36, 37

(56) References Cited

U.S. PATENT DOCUMENTS

| | | | |
|---|---|---|---|
| 1,569,778 A | | 1/1926 | Murphy |
| 1,749,368 A | | 3/1930 | Behr |
| 3,520,803 A | * | 7/1970 | Iaconneli |
| 3,552,575 A | | 1/1971 | Hultsch |
| 3,566,930 A | | 3/1971 | Kirschner |
| 3,799,353 A | | 3/1974 | Pause |
| 4,157,723 A | | 6/1979 | Granzow et al. |
| 4,223,672 A | | 9/1980 | Terman et al. |
| 4,229,290 A | * | 10/1980 | Raj |
| 4,265,280 A | | 5/1981 | Ammann et al. |
| 4,350,156 A | | 9/1982 | Malchesky et al. |
| 4,389,206 A | | 6/1983 | Bacehowski |
| 4,486,282 A | | 12/1984 | Bier |
| 4,680,025 A | | 7/1987 | Kruger et al. |
| 4,702,841 A | | 10/1987 | Sengbusch |
| 4,790,942 A | * | 12/1988 | Shmidt et al. |
| 4,844,871 A | | 7/1989 | Polaschegg |
| 5,141,592 A | * | 8/1992 | Shaposka et al. |
| 5,217,618 A | | 6/1993 | Murakoshi |
| 5,464,534 A | * | 11/1995 | Fishel |
| 5,551,942 A | | 9/1996 | Brown et al. |
| 5,656,163 A | | 8/1997 | Brown |
| 5,679,260 A | | 10/1997 | Boos |
| 5,807,492 A | | 9/1998 | Brown et al. |
| 5,858,238 A | | 1/1999 | McRea |
| 5,955,353 A | | 9/1999 | Amiot |
| 6,071,421 A | | 6/2000 | Brown |
| 6,099,730 A | * | 8/2000 | Ameer et al. |

FOREIGN PATENT DOCUMENTS

| | | |
|---|---|---|
| EP | 01076862 | 3/1989 |
| WO | WO 93/09863 | 5/1993 |

* cited by examiner

*Primary Examiner*—Joseph Drodge
(74) *Attorney, Agent, or Firm*—Connolly Bove Lodge & Hutz LLP (57) ABSTRACT

Blood is purified by removing the whole blood from a patient and feeding the blood into a manifold in a centrifuge. A purifying chamber is formed in the centrifuge from a plurality of co-arcuately arranged modules. The blood is supplied from the manifold to each of the modules. Each module contains a stack of dialysate membranes. Fresh dialysate is fed into the manifold and then to each of the modules. Under centrifugal force the cells are separated from the plasma. The plasma is purified by removing contaminants as a result of the action of the dialysate and membranes. The purified blood is returned to the patient by being fed back to the manifold and then to the patient. The used dialysate/contaminants are fed from the modules back to the manifold and out of the centrifuge.

29 Claims, 9 Drawing Sheets

SPIN-HEMODIALYSIS ASSEMBLY AND METHOD

BACKGROUND OF THE INVENTION

Hemodialysis was advanced as a life sustaining therapy for end-stage renal failure, when in about 1925 it was discovered that a thin film of re-constituted cellulose (cellophane®) had the ability to separate chemical substances while in solution by means of their unequal diffusion through a permeable membrane. This phenomenon performed particularly well with blood to differentially separate out urea molecules. Over the years there have been many changes to incrementally improve the hemodialysis process. The fundamentals, however, remained the same. Hemodialysis essentially mimics the kidney function of processing whole blood, however, man-made membranes are a poor substitute for one's kidney function.

Whole blood is made up of four major components: a) red blood cells, b) white blood cells, c) platelets, and d) plasma fluid. Since the toxins or ureas to be removed are in the plasma solution liquid portion of the whole blood, the cells just go along for the ride. The cells are also very fragile, so although they do not participate in the dialysis process directly, they do come in contact with the dialyzing membrane. Their presence, therefore, dominates the rate at which hemodialysis can proceed. Generally, a hemodialysis process takes place over a four to six hour time period for treatment and generally such treatments would be required 3 times per week. The dialyzer is also patient specific.

During each treatment the patient's total blood volume is drawn from the patient, passed through a urea separation device and returned in a continuous fashion to the patient.

Many clinical complications arise because of the need to remove urea and other toxins while the fragile cells are present: of these, compatibility of the dialyzer membranes and whole blood is of major concern. Both proteins and cells adhere to the membrane surface. This contact, in turn, causes a number of deleterious responses, which resemble those of assaults to the patient's immune system in the form of a severe allergic reactions, serious complement activation in the $C_3$ $C_5$ region, to which the body reacts as if invaded by a foreign pathogen. The responses are numerous and in some instances life threatening. They include Platelet adhesion, agglomeration and damage Thrombosis and erythrocyte adhesion Complement activation ($C_3$/$C_5$)

White cell activation (granulocytes, leukocytes, monocytes)

The clinical manifestations are also numerous and in some cases lead to morbidity and mortalities.

Anemia

Hypoxemia

Organ damage

Blood poisoning (Septicemia)

Infections, lumen and surface penetration

Malignancies

Leukopenia

SUMMARY OF THE INVENTION

It is an object of the invention to reduce or eliminate the life-threatening consequences of the basic life saving process of dialysis, while at the same time reduce the time required to cleanse the patient's blood.

It is a further object of the invention to provide an assembly and method to separate cells and plasma in such a way as to not have the cells in contact with the artificial membrane, thereby reduce the plethora of clinical problems associated with the membrane, resulting in safer and more efficient dialyzing therapy.

It is a still further object of this invention to provide such techniques for other purification purposes such as for water purification or in the processing of food or for recycling motor oil.

In accordance with this invention a fluid (such as blood) is taken from a source (such as a patient) and directed into a purifying chamber within a rotatable centrifuge. The purifying chamber includes filter structure mounted inwardly of the outer chamber wall. A fluid discharge line communicates with the purifying chamber for discharging the purified fluid after contaminants have been removed as a result of the centrifuge action. A contaminant discharge line also communicates with the purifying chamber to discharge the contaminants removed from the fluid.

In a preferred practice of the invention a purifying material (such as a dialysate) is also conveyed to the purifying chamber to assist in removing the contaminants.

In a preferred practice of the invention the purifying chamber is formed from a plurality of co-arcuate modules located at the outer wall of the centrifuge. A manifold is disposed at the center of the centrifuge. The fluid supply line, the fluid discharge line, the purifying fluid supply line and the contaminant discharge line all communicate with the manifold and further lines convey those materials from the manifold to the modules.

The invention is preferably practiced for purifying blood. In such practice blood taken from the patient is supplied to the manifold and then distributed to the individual modules. Purified blood is conveyed from the modules back to the manifold and returned to the patient. A dialysate supply line also communicates with the manifold which then distributes the dialysate to the individual modules to assist in removing contaminants such as urea. The used dialysate and contaminants are then conveyed from the modules back to the manifold and discharged from the manifold to a collector.

DETAILED DESCRIPTION

Figure 1:
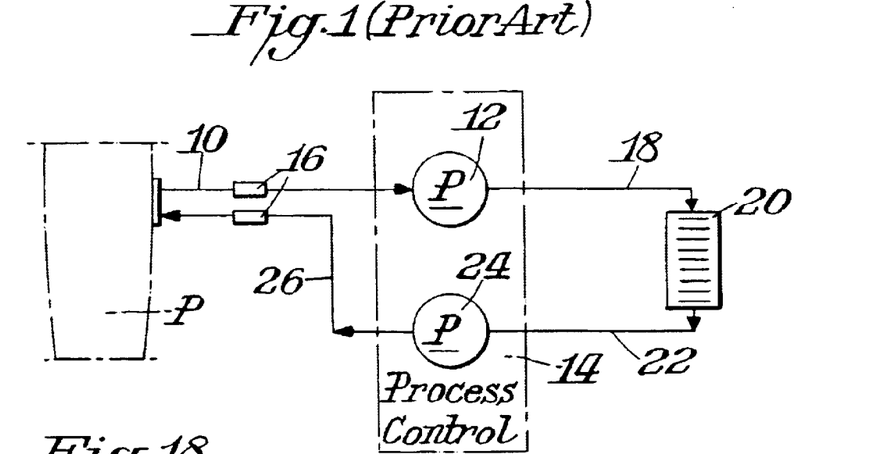
FIG. 1 is a schematic diagram representing a known hemodialysis process.

FIG. 1 represents a current prior art hemodialysis assembly. As shown therein a tube 10 is connected to the chest or arm of a patient P. A pump 12 in a process control 14 withdraws whole blood from the patient P into tube 10. The whole blood passes through a bacteria filter 16, to process control 14 and then is removed from the process control 14 through tube 18 which leads to a dialyzer 20. Dialyzer 20 may be, for example, a component commercially available from such companies as Baxter, Gambro and Fresenius. The whole blood is treated to remove contaminants in dialyzer filter 20 and the blood is then conveyed through tube 22 by means of pump 24 in process control 14. The blood is then returned to the patient P through tube 26 which incorporates a further bacteria filter 16.

The dialyzer 20 removes urea molecules from the plasma via Donan dialysis. Because, however, the red cells and the white cells or leukocytes are present, this process is hazardous in particular for the red cells which may cause cell breakdown and fracture. To avoid these problems the hemodialysis conventionally used is a slow, tedious process because of the need to protect the fragile red blood cells from damage. The use of bacteria filters is also a disadvantage in that such filters are not completely effective and also extend the time involved in the process. Such conventional process also incorporates a low pressure pump in the process control and utilizes low pressure in the dialyzer. The process described in FIG. 1 must be performed in a clinical setting which requires the patient to visit the clinics about 2 to 3 times per week for dialysis treatment that last 6 to 8 hours per visit. The inconvenience, loss of productive time for the patient, and the cost of clinic supervision all contribute to excessive costs for routine health care.

It is also known to separate the plasma from the cells by use of a centrifuge. In such practices the plasma with various contaminants such as urea would then be treated separately from the centrifuge in a dialyzer, such as dialyzer 20.

Figure 2:
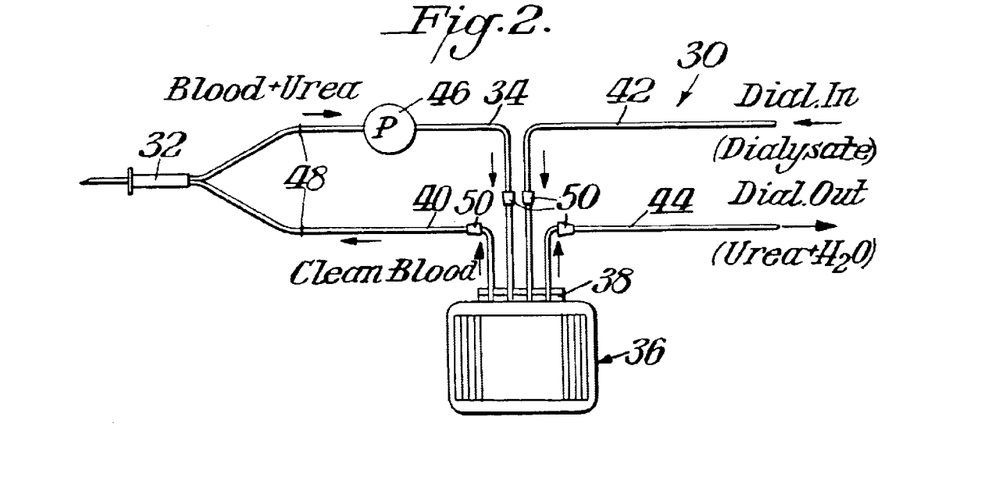
FIG. 2 is a schematic diagram representing a process in accordance with this invention as used for purifying blood.

FIG. 2 shows the system 30 in accordance with this invention. As shown therein whole blood which would contain the cells, plasma and contaminants such as urea would be removed from the patient in any suitable manner such as through catheter 32. The whole blood would be conveyed through fluid supply line 34 into a centrifuge 36. As later described the whole blood would first be conveyed into a centrally mounted manifold 38 located at the center of the centrifuge. (FIG. 2 illustrates the manifold 38 at the top of centrifuge 36, whereas the manifold would preferably be at the bottom of centrifuge 36 with the various supply and discharge lines being at the bottom of centrifuge 36.) The manifold 38 would distribute the blood to a purifying chamber at the side wall of the centrifuge. A distinctive feature of the invention is that the purifying chamber includes filter structure, such as the membranes used in known dialysizers, so that the cells would be separated from the plasma in the centrifuge and then the contaminants would be separated from the plasma as a result of the membranes. This would leave clean blood comprising the cells and plasma which would be conveyed through fluid discharge line 40 back to the patient. In the meantime, in order to assist in the removal of the contaminants or purification of the plasma a dialysate would be conveyed through dialysate supply line 42 into manifold 38 and the used dialysate would carry the contaminants and water from the centrifuge through manifold 38 to be discharged through contaminant discharge line 44 for collection at some remote location.

The invention could be broadly practiced without a manifold where the whole blood is conveyed directly to a purifying chamber at the outer wall of the centrifuge 36 and the dialysate is also conveyed to that purifying chamber. The clean blood would then be removed from the purifying chamber and directed to the patient while the used dialysate and contaminants would be discharged from the purifying chamber. For efficiency purposes, however, a manifold is used in combination with the purifying chamber being in the form of a plurality of co-arcuate modules as later described.

The assembly shown in FIG. 2 thus includes a patient catheter 32 having tubing leading from the catheter. Anticoagulated blood and urea would be pumped through tube or line 34 under the influence of blood pump 46. The clean blood would be returned through line or tube 40 back to catheter 32. Preferably, a sterile connection device 48, 48 is located in each line 34 and 40. Such sterile connection devices may also be located at other portions of the assembly such as at coupling locations 50 in lines 34, 40, 42 and 44. Such sterile connection devices may be of the type described in U.S. Pat. Nos. 4,793,880; 5,141,592; 5,256,226; 5,279,685; and 5,674,333, all of the details of which are incorporated herein by reference thereto. As used herein the term "sterile connection device" is intended to refer to a device having a pair of aligned spaced tube holders each of which has at least one tube receiving channel and includes a heated wafer located to pass between the spaced tube holders for heating plastic tubes placed therein. The connection or separation of such plastic tube is done in a sterile manner. The ability to include a sterile connection device as part of the hemodialysis system assures that the hemodialysis processes can remain totally contained and sterile. Thus, it is possible between hemodialysis sessions to seal tubes 34 and 40 at the location of the sterile connection devices 48, 48 so that the catheter could remain in the patient without the patient being immobilized as a result of connection to the rest of the assembly. Similarly, the tubings 34, 40, 42 and 44 could be sealed at the locations of couplers 50 so as to readily disconnect those components of the assembly. As a result, the centrifuge 36 with its related components could be stored separately from the other components with the various tubes extending from centrifuge 36 having sealed stub ends at the locations of the four couplers. Similarly, the dialysate supply and the contaminant/used dialysate collection components could also be located separately from the patient and from the centrifuge.

Because centrifuge 36 incorporates the dialysate membranes, as later described, the centrifuge 36 might be considered as a parallel plate spin dialyzer centrifuge.

Figure 3:
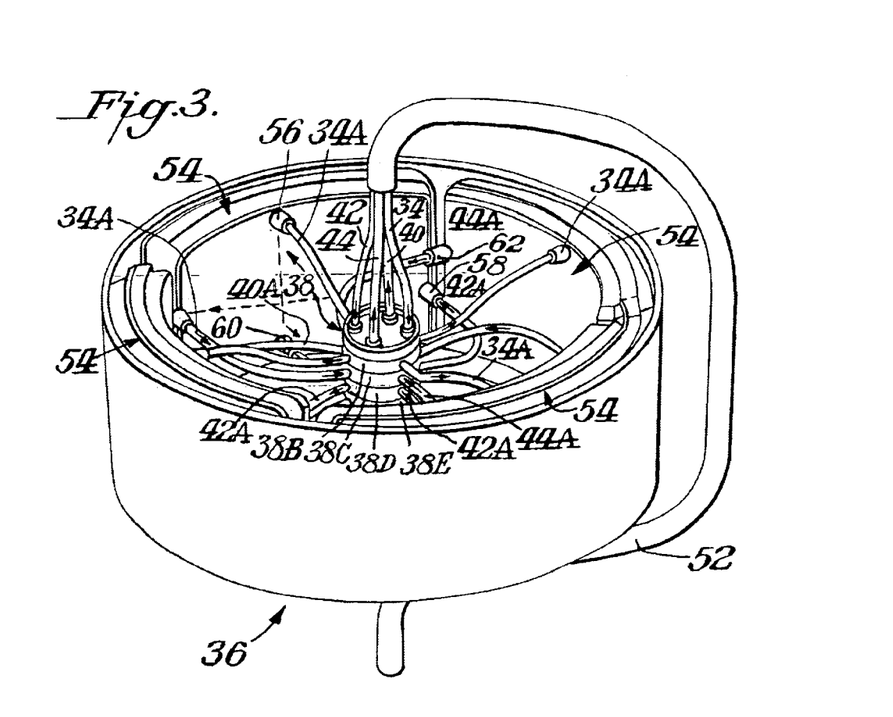
FIG. 3 is a perspective view of an inverted centrifuge in accordance with this invention.

FIG. 3 generally illustrates the construction of the parallel plate spin dialyzer centrifuge 36. FIG. 3 shows the centrifuge 36 inverted. Thus, the various supply and discharge lines enter and leave the bottom of the centrifuge 36. The various supply and discharge lines 34, 40, 42 and 44 would come together and extend along side each other within a sleeve or outer covering 52. As a result, the supply or discharge tubes or lines are maintained in a compact condition. The covering 52 would extend from above the centrifuge and then communicate with the centrifuge at the bottom of the centrifuge 36. As noted, FIG. 3 shows the centrifuge 36 inverted. In other words, what is shown at the top of FIG. 3 actually corresponds to the bottom of the centrifuge 36. Thus, FIG. 3 shows the whole blood supply tube 34 extending from covering 52 into manifold 38 as indicated by the downward arrow. The clean blood would exit from manifold 38 through line 40 as indicated by the upward arrow. The fresh dialysate enters the centrifuge 36 through line 42 which communicates with manifold 38 and the used dialysate and contaminants exit the centrifuge and manifold through line 44. The centrifuge bowl 36 and the outer cord or covering 52 are incorporated into a one omega/two omega centrifuge drive system, an established, known in the art, method of communicating to a spinning centrifuge without the use of rotating seals.

The blood is treated or purified along the outside wall of centrifuge 36 in a purifying chamber. In the preferred practice of the invention in order to increase the handling capacity and the efficiency of the blood processing the purifying chamber is formed from a plurality of individual co-arcuate modules 54. In the illustrated practice there are four such modules 54. The manifold 38 in turn is formed from a plurality of disks corresponding to the number of supply and discharge lines. In that regard a separate disk is provided to distribute the fluid of each supply and discharge line. An additional common disk is used for receiving each supply and discharge line. Thus, for example, the whole blood entering manifold 38 through supply line 34 would exit from manifold 38 from its disk 38B at four different locations, each of which is associated with a separate module 54. FIG. 3 illustrates the individual supply tubes for the whole blood designated by the reference numeral 34A as extending from manifold disk 38B to each of the four respective modules 54 at an inlet connection 56 at the top center of each module.

The dialysate supply line 42 connects with module 38 and then dialysate is fed through four individual lines 42A from manifold disk 38D to the four modules 54 at a connection 58 on the right hand edge of each module. The clean blood is returned from each module 54 through return line 40A (only one of which is seen in FIG. 3) which would extend from a connection 60 at the bottom center of each module 54 and extend back to the disk 38E of manifold 38. The clean blood would then exit the manifold through discharge line 40.

Finally, the used dialysate, urea and water would exit each module through line 44A at a connection 62 on the left-hand side of each plate and enter manifold 38 at manifold disk 38C. The contaminant and used dialysate would then be discharged from manifold 38 through line 44.

Figures 4, 5:
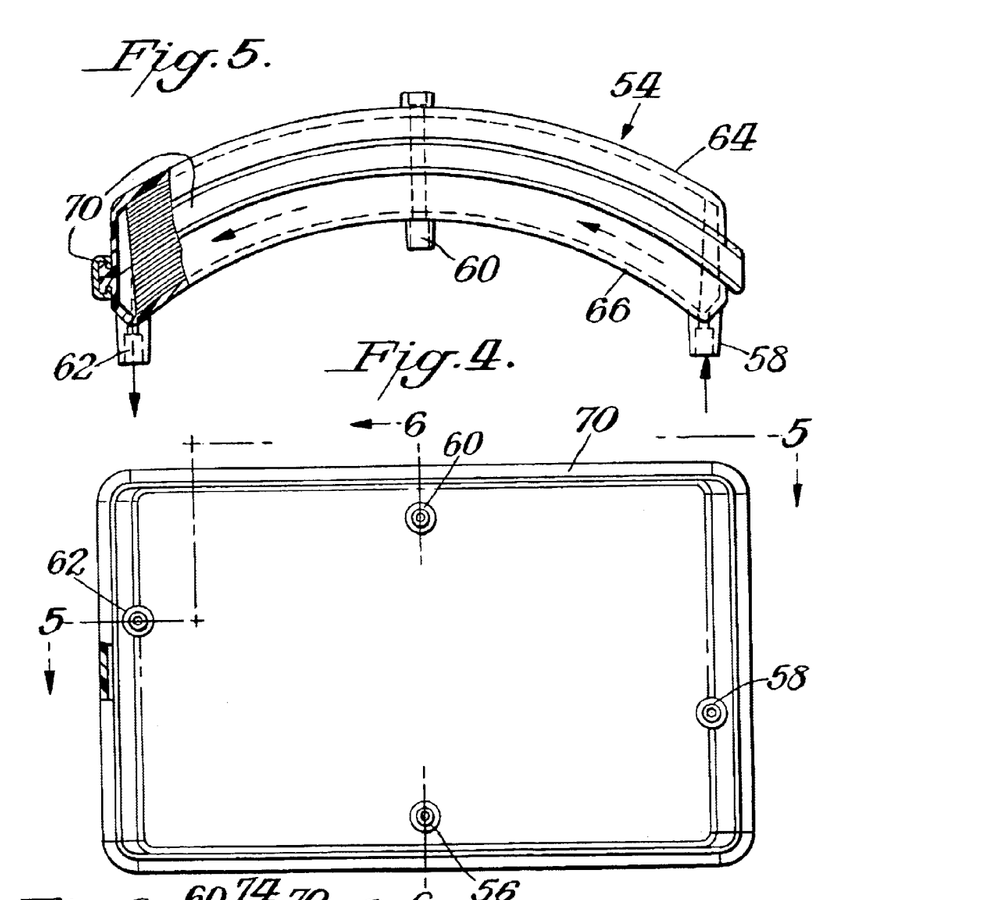
FIG. 4 is a front elevational view of a module used in the assembly of FIGS. 2–3.
FIG. 5 is a cross-sectional view taken through FIG. 4 along the line 5—5.
Figure 6:
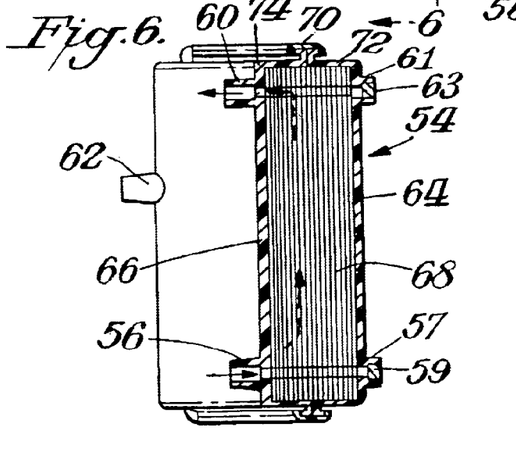
FIG. 6 is a cross-sectional view taken through FIG. 4 along the line 6—6.

FIGS. 4–6 illustrate the details of one of the modules 54. Although FIG. 3 shows the centrifuge and its components including the modules in an inverted condition, FIGS. 4–6 illustrate the modules in their normal upright condition. As shown therein, each module is a closed chamber having an arcuate or curved outer wall 64 and an inner parallel coarcuate wall 66. The outer wall 64 would be disposed against a retaining ring at the outside wall of the centrifuge 36. The various inlet and outlet nipples or connectors 56, 58, 60, 62 are located at the inner wall 66.

Whole blood would enter the module 54 through connector or nipple 56 at the bottom of the module while clean blood would be discharged through connector or nipple 60 at the top of the module with both connectors 56 and 60 being generally centrally located along the length of the module. As later described nipples 57 and 61 are located opposite nipples 56 and 60. Nipples 57 and 61 are closed by plugs 59 and 63 or by any other suitable closure such as a cap.

The fresh dialysate would enter module 54 through connector or nipple 58 while the used dialysate and contaminants such as urea would exit through connector or nipple 62 at the opposite side edge of the module.

Thus, as shown in FIG. 6 the blood entering the bottom of module 54 would flow upwardly and exit through the top as clean blood as later described. Similarly, the dialysate would enter one side of module 54 at connector 58 and exit through connector 62 taking along with it the contaminants such as urea as it exits through connector 62 as shown in FIG. 5. This will also be later described.

Each module 54 may be formed in any suitable manner such as being initially of an inner and outer shell member 72, 74 separate from each other to permit the membrane support plates 68, blood inlet/outlet distribution covers 98, and dialysis membranes 85 to be located within the purifying chamber formed by module 54. The individual shell members could then be mounted together in any suitable manner such as by a cast in place seal band 70 which connects the shell members 72, 74.

Figure 14:
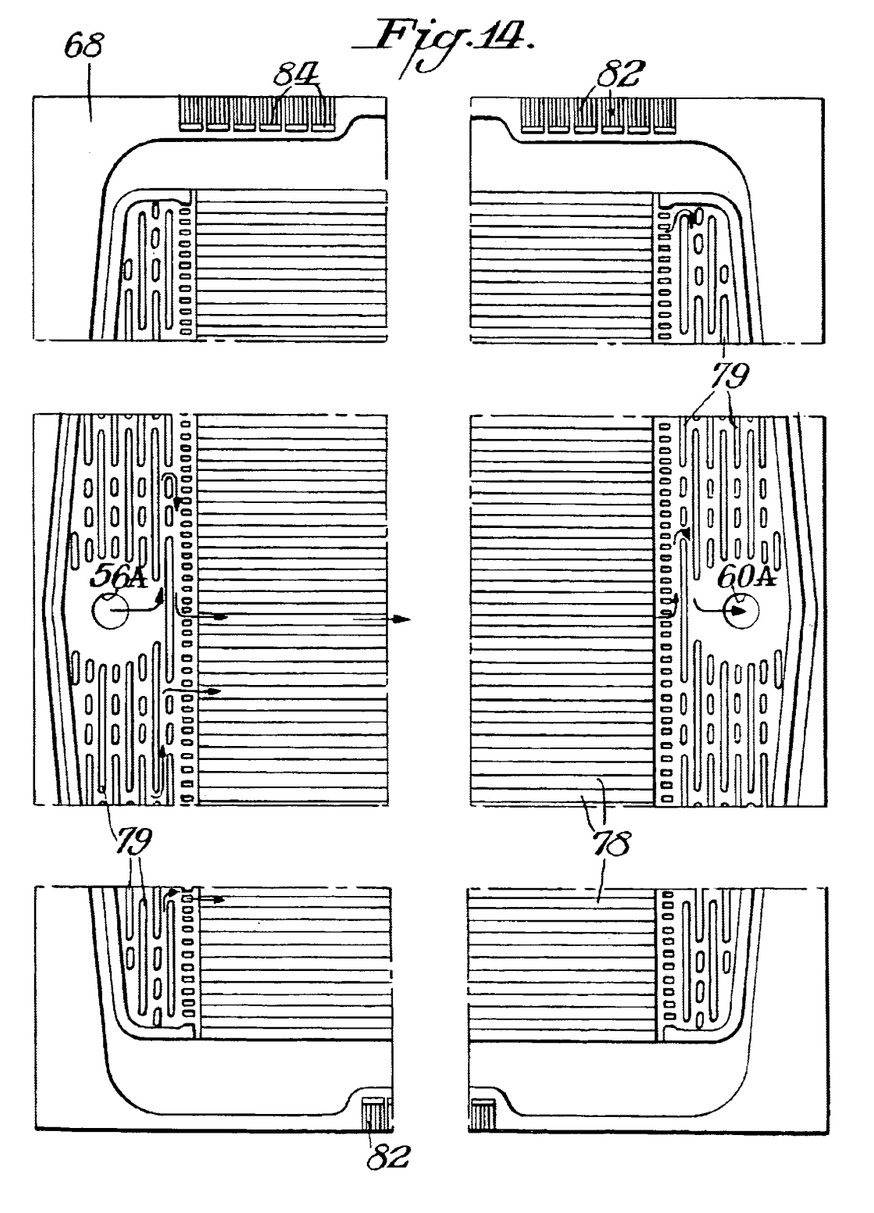
FIG. 14 is an elevational view showing a membrane support plate from the blood channel side of the membrane or filter as used in this invention.

Before the members 72, 74 are assembled together, the stack of membrane support plates, membranes and blood distribution covers must be mounted in a specific order and orientation. This may be done by temporarily placing registration rods into the inner shell member 74 through nipples 56 and 60. The inner shell member is then placed nipple end down with the registration rods facing up. The membrane support plates etc. are then fed onto registration rods through the locating holes (FIGS. 14–15) 56A and 60A. FIG. 17 illustrates the stacking order and orientation of the first two layers. The stack begins with a membrane support plate 68 placed within the inner shell member so that the blood channel side, see FIG. 14, is facing up and away from the inner member 74. Next, two blood inlet/outlet distribution covers 98 are laid over the membrane support plates covering the channels created by ribs 79 shown in FIG. 14. The filtration or dialysis membrane 85 is now fed onto the rods and laid across the blood inlet/outlet distribution covers 98 and the membrane support plate 68. The next membrane support plate is oriented blood channel side up as before, but is now rotated 180 degrees out of phase with the previous membrane support plate, before placing it on top of the membrane. The layer is completed with the addition of two more blood inlet/outlet distribution covers and another dialysis membrane. The stack continues in this fashion alternatively rotating the membrane support plates as you go. The rotation of the support plates orients the sealing ribs 97 (FIG. 16), so that each layer forms a separate and independent dialysis chamber. Finally, the outer shell member 72 is placed over the stack using the registration rods and nipple holes 57, 61 as guides. The whole assembly is then compressed and held together, while a sealing band 70 is cast in place. After the band is secured the membrane support plates 68 are compressed, sealed, and trapped in place. The registration rods can now be removed from nipples 57, 61 and closed with plugs 59, 63. Thus, nipples 57, 61 function as access openings used for assembly. The aligned holes 56A, 60A of the membrane support plates 68, blood inlet/outlet distribution covers 98, and dialysis membranes 85 form blood inlet and outlet passageways communicating with nipples 56 and 60 respectively.

Figures 7, 8, 9, 11:
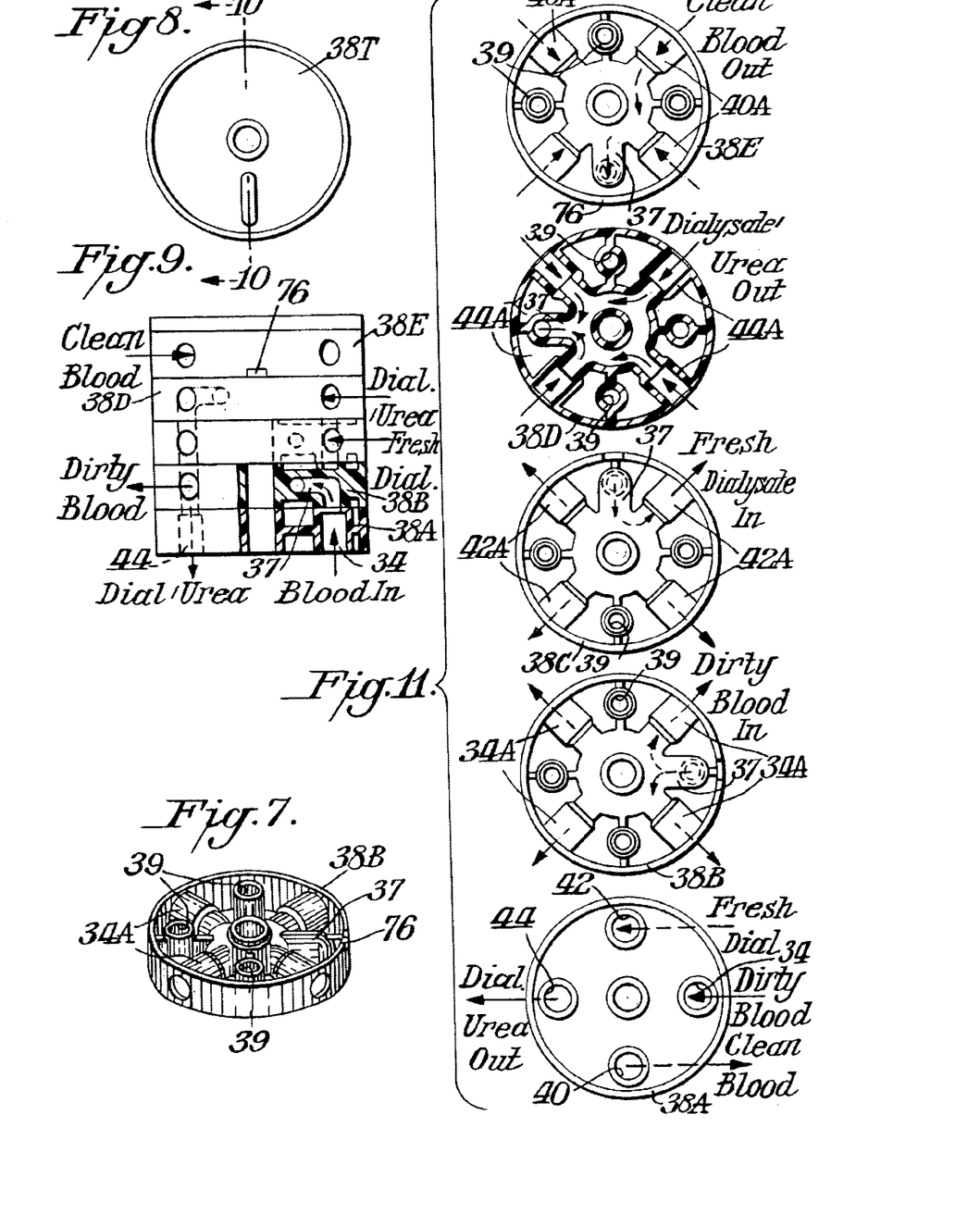
FIG. 7 is a perspective view of one of the disks in the manifold shown in FIG. 3.
FIG. 8 is a top plan view of the manifold shown in FIG. 3.
FIG. 9 is a side elevational view partly in section showing a plurality of disks which form the manifold of this invention.
FIG. 11 is an assembly view of the various disks used for forming the manifold of this invention.

The details of manifold 38 may best be understood by reference to FIGS. 7–12. Manifold 38 in general includes a plurality of disks having various passageways in the form of vertical passageways, horizontal passageways and elbows. FIG. 7, for example, illustrates one such disk 38B which is used for distributing whole blood from line 34 which would enter the manifold through disk 38A. (See FIG. 9). As shown in FIGS. 7 and 9 an elbow shaped passage 37 in disk 38B communicates with a vertical passage in disk 38A which communicates with the blood supply line 34. The blood flows into elbow passage 37 and then flows horizontally toward the center of disk 38B where the blood flows into the four horizontal passages 34A. Each horizontal passage 34A communicates with a supply line leading to a respective nipple or connector 56 of each module. Thus, the blood entering disk 38B is distributed to each of the four modules 54. If a greater or lesser number of modules is used, the same number of horizontal passageways 34A would be provided in disk 38B. Disk 38B also includes vertical passageways 39 to permit the clean blood and the fresh dialysate and the used dialysate/contaminants to pass through disk 38B through the individual passageways and into their respective disks until each vertical passageway 39 leads to an elbow passageway 37 of each respective disk 38C, 38D and 38E to permit fluid to be distributed through each of those disks.

FIGS. 9–12 show the disks in relation to each other. As shown in these figures the disks are arranged in their normal condition which is opposite to that of FIG. 3 where the disks are shown inverted since FIG. 3 is taken when looking to the bottom of the centrifuge. As illustrated the individual tubes or lines 34, 40, 42 and 44 would communicate with bottom disk 38A and the fluids would pass into or out of the various disks.

The fresh dialysate would enter disk 38A through its line 42 and would pass through vertical passage 39 in disk 38B and then enter disk 38C through elbow passage 37 and would be distributed through the four individual lines 42A into the four individual modules 54.

The used dialysate and contaminants such as urea and water would be conveyed from modules 54 through their tubes or lines 44A back to disk 38A and exit disk 38A through elbow passage 37 and then through disks 38C, 38B through aligned vertical passages 39 to be discharged from disk 38A through discharge line 44.

Finally, the clean blood would be conveyed from the individual modules 54 through lines 40A to disk 38E and then exit through elbow passage 37 and into aligned vertical passages 39 through disks 38D, 38C, and 38B and finally into disk 38A where the clean blood would be discharged through line 40 back to the patient.

Figures 10, 12:
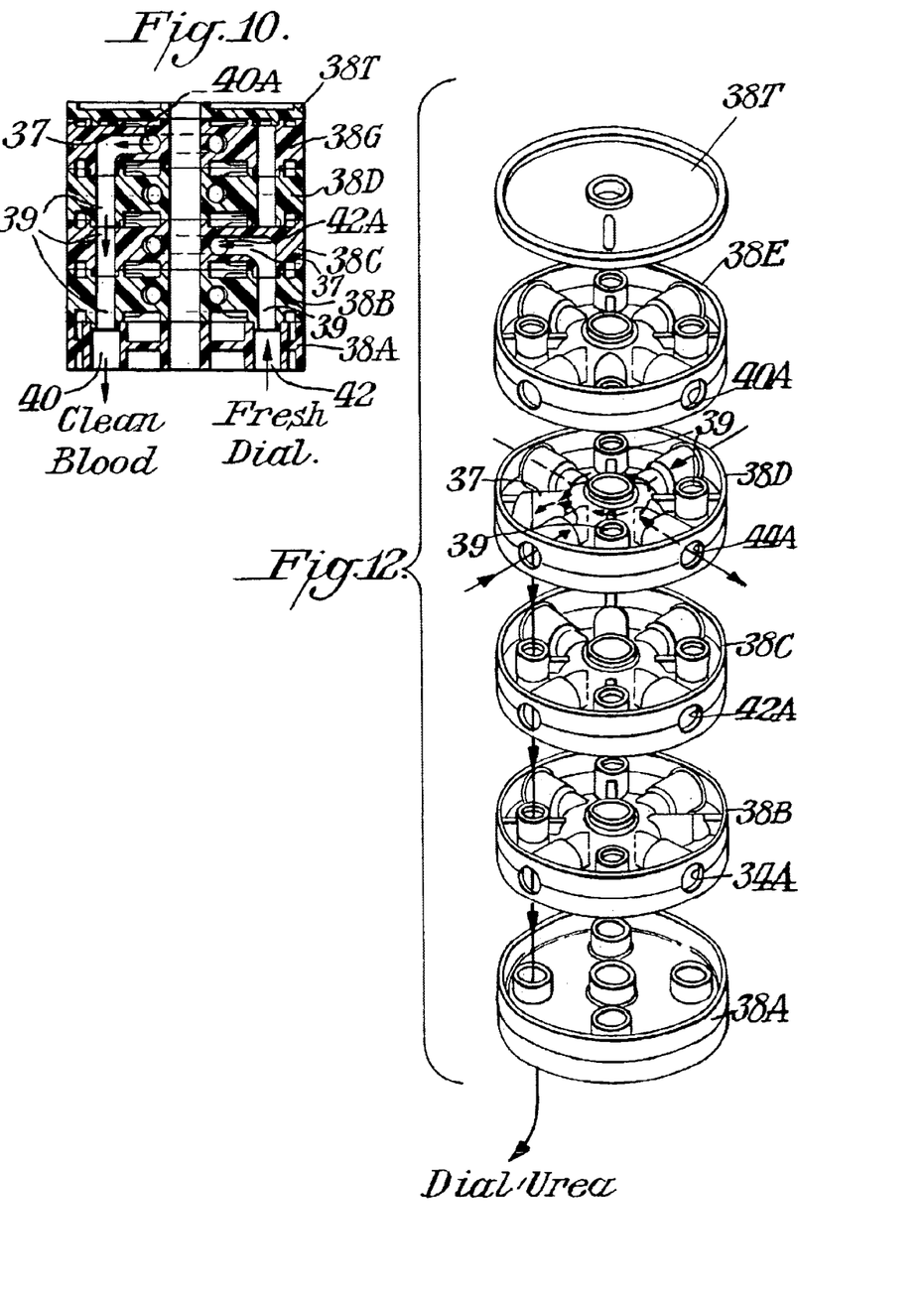
FIG. 10 is a cross-sectional view taken through FIG. 8 along the line 10—10.
FIG. 12 is an exploded view of the manifold shown in FIGS. 8–11.

FIG. 10 illustrates how by properly aligning the vertical passages 39 in the disks 38A, 38B, 38C and 38D, the clean blood flows from its line 40A to elbow passage 37 and through the various disks to be discharged through line 40. Similarly, FIG. 10 illustrates how the input of fresh dialysate through its line 42 results in flow being only through vertical passage 39 in disk 38B with the fresh dialysate being discharged from disk 38C through elbow passage 37 and then into the four lines 42A which lead to the four modules 54.

All of the disks 38A–E could be identical with each other. To facilitate the proper positioning of each disk with respect to each other, the disks could include a locating or indicating notch 76 such as shown in FIGS. 7 and 9 which would indicate the location of a particular type of passageway. Other locating or indicating structure such as marks could also be used. When the disks are properly located, the disks could be secured together in any suitable manner such as by welding.

The total number of disks for manifold 38 would be selected such that each supply or discharge line has a disk dedicated to the distribution of the fluid flowing through that line. Accordingly, since there are four supply and discharge lines 34, 40, 42, 44 there would be four disks to correspond to those four lines. In addition, there is a fifth disk 38A where the lines enter the manifold.

Although four modules are utilized in the illustrated practice of this invention, it is to be understood that the invention could also be practiced with a fewer or greater number of modules, including only a single module. Where there would only be a single module the various supply and discharge lines could go directly to the module without having to go through a manifold which distributes the fluid flowing through those lines.

By having the purifying chamber in the form of plurality of individual modules and not as one continuous 360 degree chamber, the arc length of travel of the dialysate and therefore flow resistance is reduced.

The modules can be sterilized and sealed in a case or housing made of any suitable biocompatible material such as polycarbonate.

In use the system is initially primed with saline. The fluids enter the centrifuge from the bottom, air, etc. is purged from the various tubes and lines. Blood is then introduced to the system and distributed to each module through the center manifold. The blood entering each module through nipple 56 would initially be in a turbulent stage. The blood flow is evenly divided among the stacked membrane support plates through the aligned holes 56A. The blood is then dispersed horizontally through the channels created by the raised ribs 79. During this turbulent stage the blood is protected from the dialysis membrane 85 by the blood inlet/outlet distribution cover 98. While traveling about the axis of rotation the blood is under the influence of centrifugal force and the cells begin separating from the plasma. By the time the blood reaches the perpendicular blood channels 78 and is exposed to the dialysis membrane 85, a thin plasma layer has formed above the blood cells.

Figure 13:
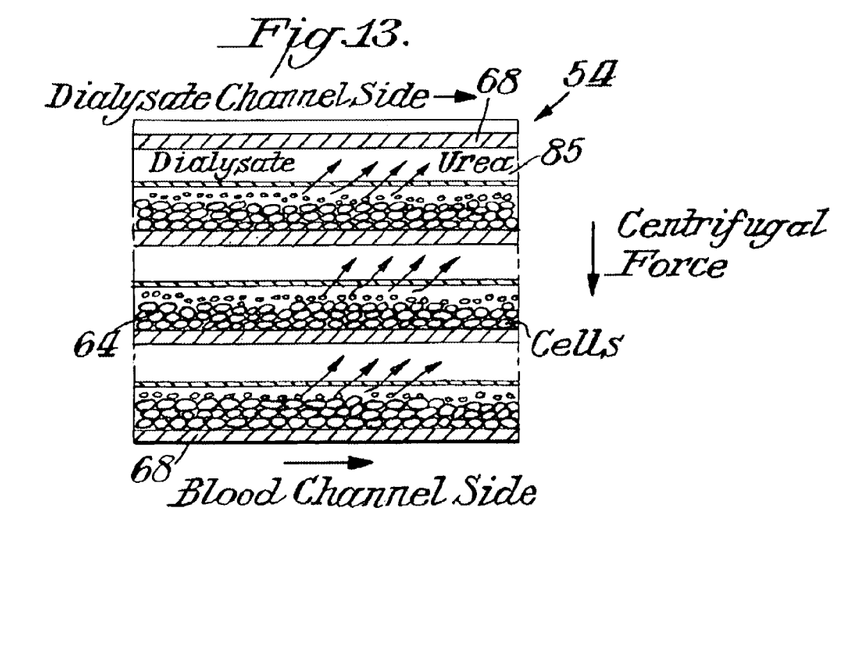
FIG. 13 is a schematic view showing the purifying action in accordance with this invention.

FIG. 13 illustrates a cross section of three sets of blood channels, membranes and dialysate interfaces. See also FIGS. 14–16. The illustration in FIG. 13 depicts the action that takes place during the blood purification process. The interface consists of a blood channel which is formed on the top (blood) side of a membrane support plate 68, followed by a dialysis membrane 85 which is held in place by dialysate channels formed on the bottom (dialysate) side of the next membrane support plate 68. The plates are stacked so that the centrifugal force is directed outwards towards the outer wall 64 of module 54 and against the bottom of the blood channels. Under the influence of centrifugal force the cells are separated from the plasma and settle towards the bottom of the blood channel 78 as they travel across the membrane support plate 68. Thus, a thin layer of plasma is formed that separates and spaces the cellular blood components from the dialysis membrane 85. Only the plasma passes by the dialysis membrane. The cells do not experience the trauma of membrane contact therefore reducing or eliminating membrane induced complement activation. The urea molecules and other uremic toxins are so small that they are unaffected by the centrifugal forces needed for blood cell separation. The dialysis function can proceed in a conventional fashion where the urea is driven by solute concentration gradients out through the cells walls across the plasma layer and through the dialysis membrane 85 into the dialysate solution. The blood that returns to the patient is virtually 100% free of urea and other toxins. This level of purity contributes to the reduced therapy time. The blood which enters the module 54 as "dirty blood" at one edge of the module at connector 56 then exits from the module at the opposite edge at connector 60 as cleaned or purified cells and plasma. See FIGS. 4 and 6 which show the flow of blood from connector 56 through the module 54 and out of connector 60.

The membranes 85 in the dialyzer plate stack are of conventional construction as is known for use in dialyzers such as in dialyzer 20 of FIG. 1. What is unique is the mounting of the membrane support plates in a centrifuge and the inclusion of covers 98, as previously described. In general, each membrane support plate 68 is an essentially rectangular plastic member having raised ribs or ridges on each side to create flow channels. FIG. 14 illustrates a membrane support plate 68 from the blood channel side. The blood channels are formed by a plurality of generally parallel spaced ribs 78 which create 132 blood channels in the illustrated embodiment extending laterally across the membrane support plate 68. The blood flows from the inlet hole 56A in the entrance side of the plate 68 and spreads in a direction perpendicular to the ribs 78 along ribs 79. The blood then flows laterally across plate 68 in the channels formed by the spaced ribs 78 into the discharge area along ribs 79 where the clean blood exits through outlet 60A.

Figure 15:
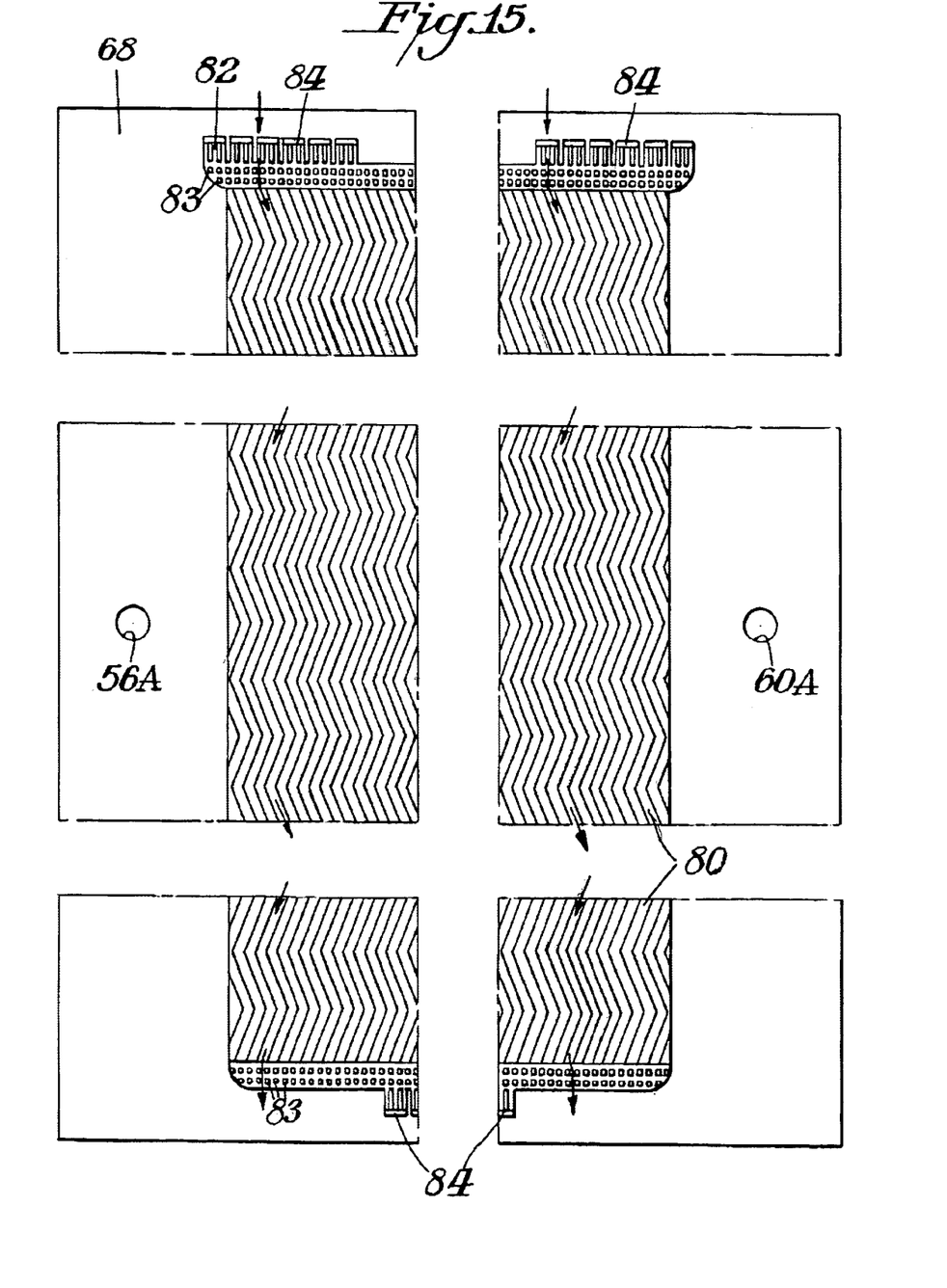
FIG. 15 is a view similar to FIG. 14 of the dialysate or purifying fluid side of the membrane support plate in accordance with this invention.

FIG. 15 illustrates the dialysate side of the membrane support plate 68. The stack of 34 membranes would include 36 membrane support plates with 34 of the plates being active and with an end plate on each side of the stack. As shown therein, a plurality of sawtooth pattern ribs 80 is formed from one side to the other across plate 68. In the illustrated embodiment 56 channels would be formed, each of which would be 1.25 mm wide covering a total distance of 70 mm whereas on the blood channel side the 132 blood channels which are each 1.25 mm wide cover a distance of 165 mm. The dialysate enters the plate 68 on the blood side in the edge channels 82, crosses over to the dialysate side through holes 84, and flows completely across the plate 68 along the raised ribs 83 and then through the channels created by ribs 80. The dialysate then exits along ribs 83, crosses back over to the blood side through holes 84 at the opposite edge channel 82. Edge 82 would correspond to connection location 58 in FIG. 5 while edge 82 on the opposite side of the support plate 68 would correspond to connector location 62 of FIG. 5.

Figure 16:
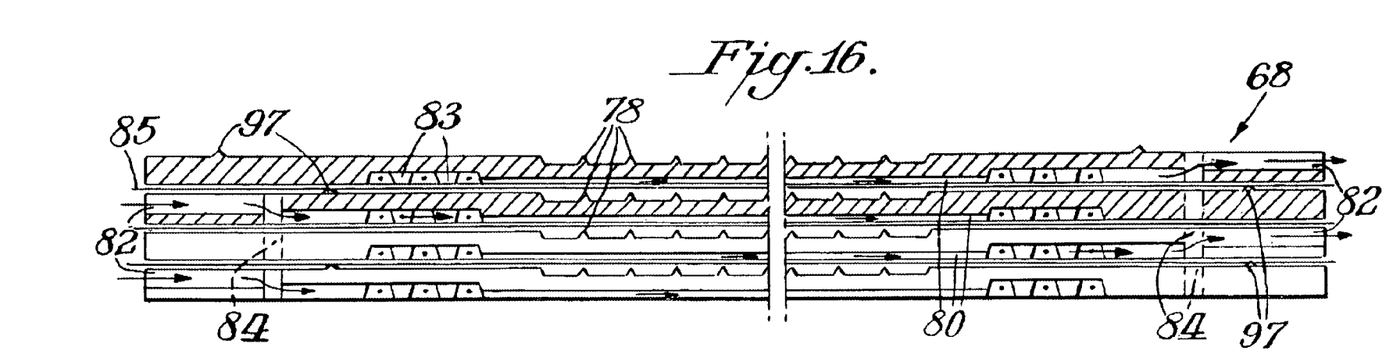
FIG. 16 is a cross-sectional view showing an alternating stack of membrane support plates and filter membranes showing the dialysate flow path in accordance with this invention.
Figure 17:
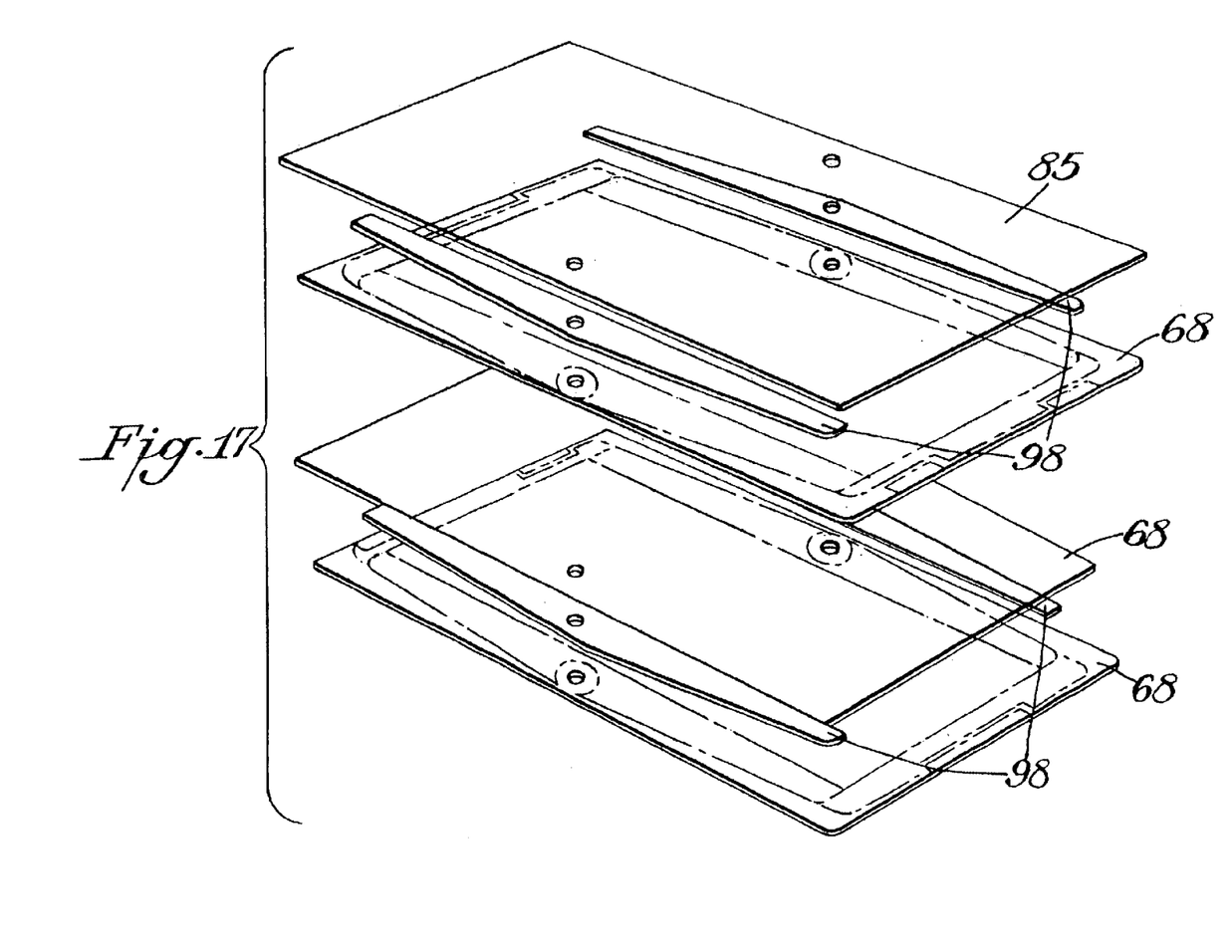
FIG. 17 is an exploded view showing the orientation and stacking order of the membrane support plates, blood inlet/outlet distribution covers, and dialysis membranes that are installed within the module shown in FIGS. 5–6.

FIG. 16 shows the pattern of flow for a stack of membranes 85 and plates 68. As shown therein the dialysate flow is passed over and under the alternating seals formed by the raised sealing ribs 97.

The raised sealing rib 97 provides an uninterrupted compression seal between the membrane support plates. The seal completely surrounds the blood channel side of the membrane support plate 68 and prevents the dialysate from directly mixing with the blood compartment. The edge channels 82, through holes 84, and the raised sealing rib 97, are arranged and interleaved so that, when the plates are alternatively rotated and stacked 180 degrees out of phase with respect to each other, a dialysate flow path is created for each individual membrane support plate.

The blood would flow in a transverse direction in the channels formed by ribs 78 perpendicular to the general direction of the dialysate flow. It is to be understood that the mechanism of purifying the plasma through the use of parallel plates is a known mechanism, but has not heretofore been used by being incorporated in a centrifuge as part of a single comprehensive system for purifying blood on a continuous basis through the use of a centrifuge for both separating the plasma from the cells and separating the contaminants from the plasma.

The invention thus makes use of known techniques such as dialyzer membranes as previously described and such as the use of centrifuges for blood separation. Reference to that regard is made to U.S. Pat. Nos. 4,680,025; 5,551,942; and 5,807,492, all of the details of which are incorporated herein by reference thereto.

Although the invention has been described with particularity to the practice of purifying blood, the same concepts can also be used for other medical purposes such as the suppression of cancer proliferation, viral infections, hepatitis therapy and liver dialysis. The invention can also be used for non-medical purposes, such as in the recycling of motor oil where advantage is taken of the fact that the impurities would be heavier than motor oil. Additional applications could include food processing, such as in the processing of beer where harsh elements are removed and in the processing of milk/soy milk. In addition, the techniques could be used for water purification on a continuous basis where the water is inputted and the heavier elements are separated. The water could pass through filters similar to the membranes 85 which are specialized filters in blood purification.

Figure 18:
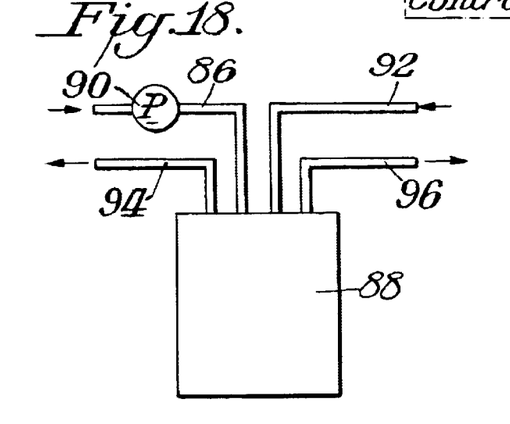
FIG. 18 is a schematic diagram showing the broad practice of this invention as used for purifying fluids in general.

FIG. 18 schematically illustrates the general practice of the invention for various techniques rather than simply blood purification. As shown therein the fluid to be purified would be fed through line 86 into centrifuge 88 as aided by pump 90. If desired, an additional purging fluid could be supplied to centrifuge 88 through line 92. Such additional purging fluid, however, would be optional. Mounted within the centrifuge 88 would be a filter system so that the fluid entering through lines 86 would be purified and removed through line 94. The contaminants removed from the purified fluid would be discharged through line 96 with or without the aid of the purging fluid from the optional line 92.

The invention thus makes use of a centrifuge to accomplish multiple stages of purification where in the purification of blood the cells are initially removed from the plasma and then the plasma is purified to remove contaminants such as urea. This takes place in such a manner which avoids the cells contacting the membranes or filter material thereby avoiding damage to the cells.

What is claimed is:

1. An assembly for purifying a fluid comprising a rotatable centrifuge, a purifying chamber in said centrifuge, filter structure in said purifying chamber for removing contaminants from the fluid, said filter structure comprising a stack of alternately arranged arcuately shared dialysate membranes and arcuately shared plates, a fluid supply line communicating with said purifying chamber for supplying the fluid to be purified, a fluid discharge line communicating with said purifying chamber for removing purified fluid from said purifying chamber, and a contaminant discharge line communicating with said purifying chamber for discharging the contaminants removed from the fluid.

2. The assembly of claim 1 including a purifying fluid supply line communicating with said purifying chamber.

3. The assembly of claim 2 wherein said assembly is used for purifying blood, and said fluid supply line feeding whole blood said fluid discharge line feeding purified blood said contaminant discharge line feeding contaminants removed from the blood said purifying fluid feeding dialysate.

4. The assembly of claim 1 wherein said assembly is used for purifying blood, said fluid supply line feeding whole blood, said fluid discharge line feeding purified blood, said contaminant discharge line feeding contaminants removed from the blood, and said purifying fluid supply line feeding dialysate.

5. The assembly of claim 4 wherein all of said membranes and plates are parallel with each other.

6. The assembly of claim 5 wherein said curved plates and membranes are stacked in a manner that creates a plurality of individual layers having the lightest components of the fluid on top and the heaviest components on the bottom whereby blood cells may separate from plasma without contacting the dialysis membrane while allowing urea contained in the plasma to pass through the dialysis membrane.

7. The assembly of claim 1 wherein said stack of plates and membranes including a plurality of plates arranged in spaced parallel relation-ship with one of said membranes between each pair of plates to form a chamber on each side of said one membrane, one of said chambers being a blood flow chamber and the other of said chambers being a dialysate flow chamber, one of said pair of plates having a blood side disposed toward said blood flow chamber, said blood side having a longitudinal central portion with blood channels extending later-ally across said central portion, a longitudinal edge portion on each side of said central portion, said edge portions having blood channels disposed longitudinally generally perpendicular to said lateral blood channels, a blood inlet communicating with one of said edge portions, a blood outlet communicating with the other of said edge portions, said other of said pair of plates being disposed toward said dialysate flow chamber and having a dialysate flow side, said dialysate flow side having a central portion with longitudinal dialysate flow channels, a cover located between said pair of plates at said longitudinal edge portions at each longitudinal side of said membrane, and said stack of plates and membranes and covers being sealed in a respective one of said modules.

8. An assembly for purifying a fluid comprising a rotatable centrifuge, a purifying chamber in said centrifuge, filter structure in said purifying chamber for removing contaminants from the fluid, a fluid supply line communicating with said purifying chamber for supplying the fluid to be purified, a fluid discharge line communicating with said purifying chamber for removing purified fluid from said purifying chamber, and a contaminant discharge line communicating with said purifying chamber for discharging the contaminants removed from the fluid, said purifying chamber comprises a plurality of co-arcuately aligned modules mounted in said centrifuge, and each of said modules having separate inlets for connection to said fluid supply line and said purifying fluid supply line and separate outlets for each of said fluid discharge line and said contaminant discharge line.

9. The assembly of claim 8 including a manifold mounted in said centrifuge, said supply lines and said discharge lines leading to and communicating with said manifold and said manifold having supply lines and discharge lines communicating with each of said modules.

10. The assembly of claim 9 wherein said manifold includes a plurality of co-axially aligned disks, each of said disks having a plurality of passages which are alignable with passages of the other of said disks whereby a flow passage may selectively be created between said supply and discharge lines entering said manifold, and said supply and discharge lines connecting said manifold with said modules.

11. The assembly of claim 10 wherein a separate one of each of said disks functions to distribute the fluid for a separate one of said supply lines and discharge lines.

12. The assembly of claim 11 wherein said disks are identical to each other.

13. A The assembly of claim 12 wherein said disks includes indicating structure to facilitate proper alignment of said disks.

14. The assembly of claim 9 wherein each of said modules comprises a closed chamber having an arcuate inner wall and a coarcuate outer wall, said inlet for said fluid supply line being located in said inner wall opposite said outlet for said fluid discharge line in said inner wall, and said inlet for said purifying fluid supply line being located in said inner wall opposite said outlet for said contaminant discharge line in said inner wall.

15. The assembly of claim 4 wherein said filter structure is a stack of alternately arranged dialysate plates and membranes.

16. The assembly of claim 15 wherein each of said modules is formed from a first shell member peripherally connected to a second shell member, said inner wall being part of said first shell member, said outer wall being part of said second shell member, and each of said plates having a hole in line with said outlet for said fluid discharge line.

17. The assembly of claim 16 wherein said outer wall has an access opening in line with said holes in said membranes, and a closure closing said access opening.

18. The assembly of claim 15 wherein said stack of plates and membranes includes a plurality of plates arranged in spaced parallel relationship with one of said membranes between each pair of plates to form a chamber on each side of said one membrane, one of said chambers being a blood flow chamber and the other of said chambers being a dialysate flow chamber, one of said pair of plates having a blood side disposed toward said blood flow chamber, said blood side having a longitudinal central portion with blood channels extending laterally across said central portion, a longitudinal edge portion on each side of said central portion, said edge portions having blood channels disposed longitudinally generally perpendicular to said lateral blood channels, a blood inlet communicating with one of said edge portions, a blood outlet communicating with the other of said edge portions, said other of said pair of plates being disposed toward said dialysate flow chamber and having a dialysate flow side, said dialysate flow side having a central portion with longitudinal dialysate flow channels, a cover located between said pair of plates at said longitudinal edge portions at each longitudinal side of said membrane, and said stack of plates and membranes and covers being sealed in a respective one of said modules.

19. The assembly of claim 18 wherein said longitudinal dialysate flow channels have a sawtooth flow pattern, each of said plates having flow channels at each end thereof on each side of said plate, said flow channels at one end being in a centrally located set, said flow channels at the other end being in two spaced sets, holes extending through said plate to create communication between said flow channels on each side of said plate whereby dialysate may flow through said plate and enter said two spaced sets of flow channels and then flow through said longitudinal flow channels and then into said centrally located set of flow channels, and each of said plates being disposed in a position rotated 180° with respect to its adjacent plate.

20. The assembly of claim 9 wherein said manifold includes a plurality of co-axially aligned disks, each of said disks having a plurality of passages which are alignable with passages of the other of said disks whereby a flow passage may selectively be created between said supply and discharge lines entering said manifold and said supply and discharge lines connecting said manifold with said modules.

21. The assembly of claim 20 wherein a separate one of each of said disks functions to distribute the fluid for a separate one of said supply lines and discharge lines.

22. The assembly of claim 8 wherein there are four of said modules forming a 360° arc.

23. The assembly of claim 8 including a manifold mounted in said centrifuge, said supply lines and said discharge lines leading to and communicating with said manifold, and said manifold having supply lines and discharge lines communicating with each of said modules.

24. A dialyzer for purifying blood comprising a module having a stack of alternately arranged arcuately shared dialysate plates and arcuately shaped membranes, said stack of plates and membranes including a plurality of plates arranged in spaced parallel relation-ship with one of said membranes between each pair of plates to form a chamber on each side of said one membrane, one of said chambers being a blood flow chamber and the other of said chambers being a dialysate flow chamber, one of said pair of plates having a blood side disposed toward said blood flow chamber, said blood side having a longitudinal central portion with blood channels extending laterally across said central portion, a longitudinal edge portion on each side of said central portion, said edge portions having blood channels disposed longitudinally generally perpendicular to said lateral blood channels, a blood inlet communicating with one of said edge portions, a blood outlet communicating with the other of said edge portions, said other of said pair of plates being disposed toward said dialysate flow chamber and having a dialysate flow side, said dialysate flow side having a central portion with longitudinal dialysate flow channels, a cover located between said pair of plates at said longitudinal edge portions at each longitudinal side of said membrane, and said stack of plates and membranes and covers being sealed in said module.

25. A dialyzer for purifying blood comprising a module having a stack of alternately arranged dialysate plates and said stack of plates and membranes including a plurality of plates arranged in spaced parallel relationship with one of said membranes between each pair of plates to form a chamber on each side of said one membrane, one of said chambers being a blood flow chamber and the other of said chambers being a dialysate flow chamber, one of said pair of plates having a blood side disposed toward said blood flow chamber, said blood side having a longitudinal central portion with blood channels extending laterally across said central portion, a longitudinal edge portion on each side of said central portion, said edge portions having blood channels disposed longitudinally generally perpendicular to said lateral blood channels, a blood inlet communicating with one of said edge portions, a blood outlet communicating with the other of said edge portions, said other of said pair of plates being disposed toward said dialysate flow chamber and having a dialysate flow side, said dialysate flow side having a central portion with longitudinal dialysate flow channels, a cover located between said pair of plates at said longitudinal edge portions at each longitudinal side of said membrane, said stack of plates and membranes and covers being sealed in said module, said longitudinal dialysate flow channels having a sawtooth flow pattern, each of said plates having flow channels at each end thereof on each side of said plate, said flow channels at one end being in a centrally located set, said flow channels at the other end being in two spaced sets, holes extending through said plate to create communication between said flow channels on each side of said plate whereby dialysate may flow through said plate and enter said two spaced sets of flow channels and then flow through said longitudinal flow channel and then into said centrally located set of flow channels, and each of said plates being disposed in a position rotated 180° with respect to its adjacent plate.

26. A method of purifying a fluid comprising supplying the fluid to be purified into a purifying chamber in a centrifuge, disposing filter structure in the centrifuge, rotating the centrifuge to separate lighter components of the fluid from heavier components of the fluid, filtering contaminants from the heaver components of the fluid by passing the heavier components of the fluid through the filter structure, discharging the purified fluid from the centrifuge, discharging the contaminants from the centrifuge, wherein the fluid to be purified is blood and the filter structure is a stack of dialysate membranes, the lighter components of the fluid being the cells of the blood and the heavier components being the plasma, feeding fresh dialysate into the purifying chamber to remove contaminants from the plasma, discharging the used dialysate with the contaminants which have been removed from the plasma, wherein the purifying chamber is in the form of a plurality of co-arcuately arranged modules, feeding the whole blood and the dialysate into a manifold and then to the modules, and removing the purified blood and used dialysate/contaminants from the modules to the manifold and out of the centrifuge.

27. The method of claim 26 wherein the manifold includes a plurality of coaxially aligned disks having alignable passageways, and utilizing a separate disk to distribute the whole blood to the modules and a further separate disk to distribute the dialysate to the modules and a further separate disk to collect and discharge the purified blood and a further separate disk to collect and discharge the used dialysate/contaminants.

28. The method of claim 27 wherein the whole blood is removed from a patient through a catheter and the purified blood is fed into the patient through the catheter on a continuous basis.

29. The method of claim 26 wherein the blood is removed from a patient and supplied to the centrifuge through a supply tube, the purified blood being returned from the centrifuge to the patient through a discharge tube, periodically cutting through and sealing the supply tube and the discharge tube by a sterile connection device, and reconnecting and opening the sealed supply tube and discharge tube from the patient to a corresponding supply tube and discharge tube from the centrifuge by a sterile connection device.

* * * * *